United States Patent [19]

Porat et al.

[11] Patent Number: 4,807,364
[45] Date of Patent: Feb. 28, 1989

[54] MEDICAL SCISSORS

[76] Inventors: Michael Porat, 52 Hamitnadev Str., Tel Aviv 69690, Israel; Amir Porat, 18 Highland Dr., North Coldwell, N.J. 07006

[21] Appl. No.: 34,592

[22] Filed: Mar. 27, 1987

[51] Int. Cl.[4] ............................................. B26B 13/04
[52] U.S. Cl. ....................................... 30/268; 30/254; 30/341
[58] Field of Search ................. 30/254, 260, 266, 268, 30/341

[56] References Cited

U.S. PATENT DOCUMENTS

| | | | |
|---|---|---|---|
| 1,031,370 | 7/1912 | Putney | 30/268 |
| 3,688,402 | 9/1972 | Shannon | 30/266 X |
| 3,750,282 | 8/1973 | Eaton et al. | 30/341 X |
| 4,007,524 | 2/1977 | Hannes et al. | 30/266 |
| 4,062,113 | 12/1977 | Ishida et al. | 30/260 |

Primary Examiner—Frank T. Yost
Assistant Examiner—Michael D. Folkerts
Attorney, Agent, or Firm—Dennison, Meserole, Pollack & Scheiner

[57] ABSTRACT

Disposable scissors for medical use comprising two plastic handles, two shaped stainless steel blades disposed between the handles and in contact with each other, pivot means coupling the handles and the blades, characterized in that the part of each handle through which the pivot extends defines an integral extension extending from the pivot outward over part of the blades to support and apply pressure thereon during the shearing movement.

3 Claims, 1 Drawing Sheet

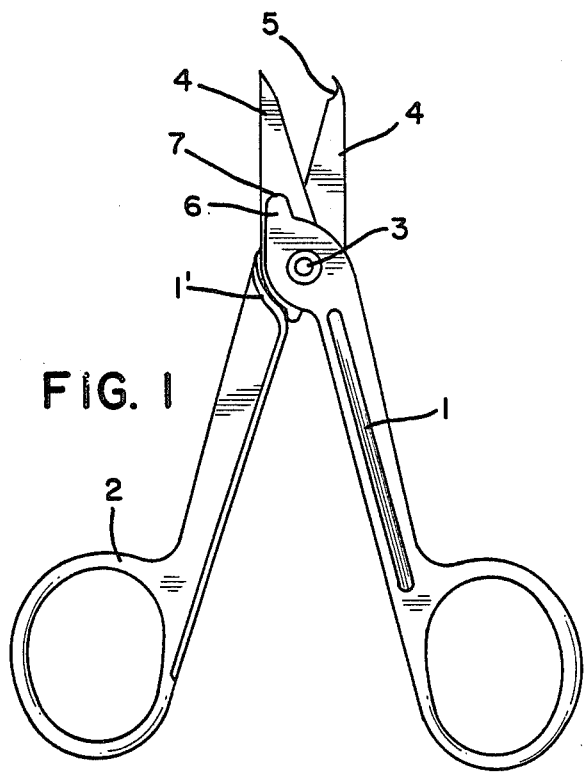
FIG. 1
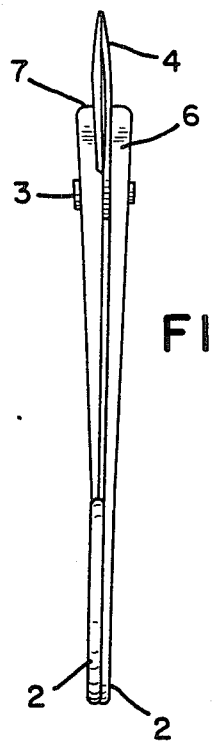
FIG. 2
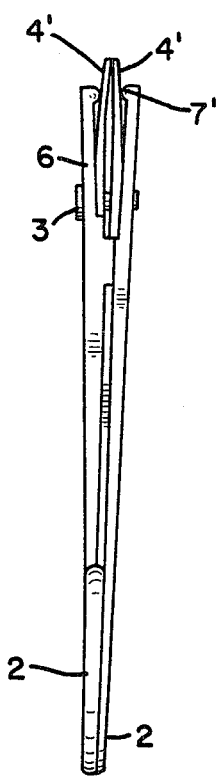
FIG. 4
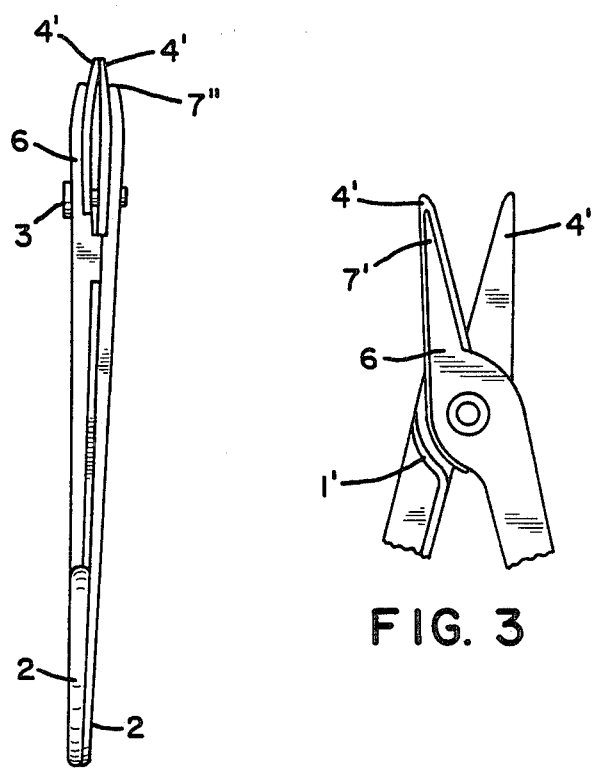
FIG. 3
FIG. 5

MEDICAL SCISSORS

FIELD OF THE INVENTION

The present invention concerns disposable scissors for medical use.

BACKGROUND OF THE INVENTION

Scissors for medical use were, up to a short time ago, made of stainless steel intended to be sterilized for repeated use. However, even with sterilization, the problem of infection exists. In order to overcome this problem, disposable scissors were produced. These are generally constituted by short stainless steel blades attached to the pivot of plastic handles.

An example of such scissors is described and claimed in German Patent publication No. 3,212,124 which discloses surgical scissors with disposable blades which can be attached and detached from the handles. The handles are not disposable and require sterilization for reuse.

Many of these prior art scissors suffer from the disadvantage that the pivot thereof retains the blades in intimate contact, thereby trapping bacteria and preventing penetration of sterilization steam or fluid.

An effort to overcome this problem is described and claimed in U.S. Pat. No. 3,688,402 to Shannon. Each blade of the scissors of Shannon comprises a flat mounting part at the pivot, an outer blade or cutting part which is at a slight angle to said flat part, and an inner camming part at an angle to the flat part which is slightly greater than the angle of the blade part and has a stop means at its outer end. The shape of the blades assures that when the handles are closed, the blades come into pointwise contact with each other along their cutting edges during the shearing action. Yet, when the scissors are closed, a space is defined between the blades at the pivot to permit effective sterilization.

There are also known in U.S. Pat. No. Des. 285,167 and Israel Design Registrations Nos. 9605, 9606, and 9607 to the present applicants, disposable scissors of this kind wherein the handle is provided with a triangular extension extending from the pivot in the direction of the blade.

These prior art scissors having pointwise shearing action suffer from the disadvantage that the blades are loosely supported on the handles around the pivot point with which the handles are connected to each other. This often causes impaired shearing action. Furthermore, the blades are relatively thin and can bend under the stress of cutting a hard object.

SUMMARY OF THE INVENTION

It is an object of the present invention to provide disposable scissors which overcome the disadvantages of the above-mentioned prior art.

There is thus provided in accordance with the present invention disposable scissors for medical use of the kind having plastic handles and including a part through which the pivot extends, stainless steel blades being held on the pivot in contact with each other, characterized in that said part of each handle is provided with an integral extension which lies over part of the blades and supports them during the shearing movement.

According to a preferred embodiment, the extension is thicker at its outer end than at the part surrounding the pivot. According to an alternate embodiment, the extension is curved from the pivot to its outer end.

BRIEF DESCRIPTION OF THE DRAWINGS

The present invention is illustrated, by way of example only, in the accompanying drawings in which:

FIG. 1 is a plan view of disposable scissors for medical use constructed and operative in accordance with the invention;

FIG. 2 is an side view of the scissors of FIG. 1 in the closed orientation;

FIG. 3 is a plan view of a detail of a second embodiment thereof;

FIG. 4 is an side view of the scissors of FIG. 3 in the closed orientation; and

FIG. 5 is an side view of disposable scissors constructed and operative in accordance with an alternate embodiment of the invention.

DETAILED DESCRIPTION OF THE INVENTION

The disposable scissors according to the invention comprise two handles 1 of plastics having the usual finger grips 2. Handles 1 are connected to each other around pivot 3 as by a rivet. Two stainless steel blades 4 of known shape are disposed between handles 1 and coupled thereto by pivot 3. Preferably, blades 4 are each disposed against an integral ridge 1' on the inside of its corresponding handle 1.

As illustrated in FIGS. 1 and 2, one of the blades 4 has the known depression 5 near the end of its cutting edge for suture removal. Alternately, the blades may be of any conventional shape. For example, in the embodiment of Figs. 3 and 4, blades 4' are identical and are both sharp. Both blades may also be blunt or one may be sharp and one blunt, as dictated by the purpose for which they are destined.

Preferably, the blades 4 define a slight curve towards one another, as known. This serves to provide sharper cutting due to the single point cutting action.

According to the invention, the part of the handle 1 through which pivot 3 passes has an integral extension 6 which lies over part of the outside or outer surfaces of the blades 4 and supports them during the cutting action. It will be appreciated that the extension 6 must extend beyond the radius of the part surrounding the pivot 3, but the actual amount of the surface of blades 4 to be covered depends upon the shape of the blades and the precise use of the scissors. Thus, in some cases, extension 6 may cover substantially all of the blade except the cutting edge, as shown in FIG. 3, while in others, it preferably defines a rounded tooth as illustrated in FIG. 1. In any event, it must not interfere with the cutting ability of the scissors or detract from the ease of insertion of the blades into small or narrow areas in the body which are to be cut.

According to one embodiment of the invention, the thickness of extension 6 is greater at its outer end 7 than at the part surrounding pivot 3 and merging with handle 1, as illustrated in FIG. 2. The thickness increases gradually from the part around pivot 3 to end 7, but at a greater angle than the angle of the blade part of the blades 4. The actual thickness of the outer tip 7 also depends on the final use of the scissors and need only be sufficient to provide support for the blades during cutting.

According to an alternate embodiment, illustrated in FIG. 4, extension 6 defines a protrusion 7' at the point of contact with the blades than at the pivot. The added thickness at the contact point 7' serves to support the blades.

According to another alternate embodiment, illustrated in FIG. 5, extension 6 is of constant thickness but defines a curve from the pivot to its outer end 7".

As long as the scissors are in the open state, the blades 4 are loose, but when the scissors are being closed, the pressure of extension 6 in each embodiment presses on each blade so that they are forced onto each other in single point contact along the cutting edge. Owing to the support by extension 6 of these blades, they are urged towards each other during cutting whereby sure and improved shearing action is obtained.

If desired, the handle can be made of steam autoclavable plastic with or without reinforcement, as known in the plastic industry.

It will be appreciated by those skilled in the art that the present invention is not limited to what has been shown and described hereinabove. Rather, the scope of the invention is limited solely by the claims which follow.

We claim:

1. In disposable scissors for medical use comprising two plastic handles, two shaped stainless steel blades disposed between said handles and in contact with each other, and pivot means coupling said handles to said blades for pivotal movement of said blades into mutual cutting engagement, said blades extending forward of said pivot means and terminating in free forward ends, each of said handles, at the pivot means, being immediately laterally outward of a corresponding one of said blades; the improvement comprising an integral extension on each handle extending from the pivot means forward over part of the corresponding blade and immediately outward thereof, each said extension terminating in a forward end forwardly spaced from said pivot means, each said extension including integral pressure means freely engaged inwardly against the outer surface of the corresponding blade at said forward end and in forwardly spaced relation to said pivot means for applying pressure to the blade generally perpendicular to the pivoted movement of the blades said pressure means comprising a greater thickness and an inward enlargement of said extension relative to the thickness of the corresponding handle around the pivot means.

2. Disposable scissors according to claim 1 wherein said pressure means of each extension includes an inwardly directed protrusion at the forward end of the extension.

3. In disposable scissors for medical use comprising two plastic handles, two shaped stainless steel blades disposed between said handles and in contact with each other, and pivot means coupling said handles to said blades for pivotal movement of said blades into mutual cutting engagement, said blades extending forward of said pivot means and terminating in free forward ends, each of said handles, at the pivot means, being immediately laterally outward of a corresponding one of said blades; the improvement comprising an integral extension on each handle extending from the pivot means forward over part of the corresponding blade and immediately outward thereof, each said extension terminating in a forward end forwardly spaced from said pivot means, each said extension including integral pressure means freely engaged inwardly against the outer surface of the corresponding blade at said forward end and in forwardly spaced relation to said pivot means for applying pressure to the blades generally perpendicular to the pivoted movement of the blades, each said extension defining a curve from the pivot means to the forward end of the extension and being generally spaced from the corresponding blade between the pivot means and said forward end of the extension.

* * * * *